United States Patent [19]

Coles et al.

[11] Patent Number: 5,063,509

[45] Date of Patent: Nov. 5, 1991

[54] METHOD FOR DETERMINING DENSITY OF SAMPLES OF MATERIALS EMPLOYING X-RAY ENERGY ATTENUATION MEASUREMENTS

[75] Inventors: Mary E. Coles, Addison; Ernest L. Muegge, Grand Prairie, both of Tex.

[73] Assignee: Mobil Oil Corporation, Fairfax, Va.

[21] Appl. No.: 470,478

[22] Filed: Jan. 26, 1990

[51] Int. Cl.$^5$ .............................................. G01D 18/00
[52] U.S. Cl. ................................... 364/420; 250/269; 73/153
[58] Field of Search ............................... 364/420–421; 378/5; 250/252.1, 253, 255, 265, 269; 73/153

[56] References Cited

U.S. PATENT DOCUMENTS

4,542,648  9/1985  Vinegar et al. ...................... 73/153
4,571,491  2/1986  Vinegar et al. ................. 250/252.1

*Primary Examiner*—Gail O. Hayes
*Attorney, Agent, or Firm*—Alexander J. McKillop; Charles J. Speciale; George W. Hager, Jr.

[57] ABSTRACT

X-ray attenuation measurements at two or more energies are carried out on core samples of earth materials for use in determining relative Compton scattering and photoelectric contributions to attenuation. The measurements are utilized to calculate material bulk density from the change in attenuation between such dual X-ray energies and the attenuation for one of the dual X-ray energies.

10 Claims, 5 Drawing Sheets

METHOD FOR DETERMINING DENSITY OF SAMPLES OF MATERIALS EMPLOYING X-RAY ENERGY ATTENUATION MEASUREMENTS

BACKGROUND OF THE INVENTION

Computed tomography (CT) technology has been in use in the medical field for several years. Such CT scanning instruments produce a cross-sectional view through the subject material along any chosen axis. A two dimensional X-ray image of electron density variations within the object scanned is produced. The advantages of CT scanning over conventional radiography is found in its much clearer images and its superior density resolution. In medical CT scanners, an X-ray source and a dectector array circle a patient in a period of about 2 to 9 seconds and produce an image with maximum resolutions of 0.25 mm in the X-Y plane. This plane can be moved in discrete intervals to obtain information in 3 dimensions. For more details of such medical CT scanners, reference may be made to U.S. Pat. No. 4,157,472 to Beck, Jr. and Barrett (assignee General Electric Company) and U.S. Pat. No. 4,399,509 to Hounsfield (assignee EMI Limited).

Many other applications of CT scanning can also be made. For example, CT scanning has been applied to the non-destructive testing of wood materials, such as for disease in living trees, see U.S. Pat. No. 4,283,629 to Habermehl. In a yet further application, CT scanning has ingots, pipes, etc. see U.S. Pat. No. 4,422,177 to Mastronardi et al. (assignee American Science and Engineering, Inc.). More recently, the CT scanning technology has been applied to the field of energy research by way of petrophysical and reservoir engineering applications, see an article entitled "X-ray computerized Tomography", Journal of Petroleum Technology, pages 885–898, August, 1987.

Processes involved in coal gasification and combustion have been monitored using time-lapse CT imagery to observe changes in density (e.g., thermal expansion, fracturing, emission of gases, consumption of combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid fronts. By subtracting the images of the cores before and after flooding, the exact shapes of the fluid front was determined. Such core flood experiments allows the interior of the core sample to be observed without disturbing the sample. The sweep efficiency and flow paths of fluid of interest may now be studied on the scale of millimeters. The penetration of X-rays allows experiments to be performed with up to 4 inch diameter core samples.

Drilling fluids can be analyzed by CT scanning as such fluids are characterized by high density brines, various organics and several compositionally different weighing agents. Formation damage can be investigated since CT scanning can detect migration of clays, absorption of organics and the reversibility of completion fluid penetration. Shale oil recovery can be aided as CT scanning could detect penetration by solvents and could directly measure structure changes on retorting. Rock fractures can be identified.

U.S. Pat. No. 4,649,483 to Dixon discloses a method for determining fluid saturation in a porous media through the use of CT scanning. Multi-phase fluid saturation in a sample of a porous media is determined through computer tomographic scanning. The sample is scanned with X-rays of differing energies in both the fluid saturated and the fluid extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined.

U.S. Pat. No. 4,688,238 (issued Aug. 18, 1987, to Sprunt et al. discloses a method for using CT scanning over a range of confining pressures on a core sample to determine pore volume change, pore compressibility and core fracturing. A core sample with a surrounding elastic jacket is placed in a confining pressure cell. Pressure is applied to the cell to press the jacket into contact with the surface of the sample. The pressure in the cell is increased stepwise over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which pore volume and pore compressibility of the sample are measured without being affected by improper conformance of the jacket to the surface of the sample. Also rock fracturing is determined from the pressure at which crushing of the sample destroys permeable channels within the sample and results in a permeability of the sample.

U.S. Pat. No. 4,722,095 issued Jan. 26, 1988 to Muegge et al. discloses a method for identifying porosity and drilling mud invasion of a core sample from a subterranean formation. A gas is supplied to the core sample at a first pressure. The gas is thereafter allowed to expand from the core sample until equilibrium is reached. The volume of the gas which expands from the core sample is measured. A second pressure is measured in the core sample after the gas has expanded. The pore volume of the core sample is determined from such first and second pressures and such measured gas volume. Bulk volume of the core sample is measured. Porosity of the core sample is determined from the ratio of the pore volume to the bulk volume. The core sample is scanned with X-rays and computed tomographic images produced. The concentration of drilling mud solids in the core sample is identified from the density effect of the drilling mud solid on the computed tomographic images. The porosity determination is corrected for the volumetric concentration of drilling mud solid in the pore spaces of the core sample. The X-ray scanning is calibrated to a density scale based on the barite content of the drilling mud, the barite having a higher grain density than the remaining minerals forming the core sample. This X-ray scanning is preferably calibrated by adjusting the computed tomographic number scale in Hounsfield units to a zero level based on the numerical measure of the X-ray absorption property of barite.

U.S. Pat. No. 4,799,382 issued Jan. 24, 1989 to Sprunt et al. discloses a method for measuring reservoir characteristics of a core sample from a subsurface formation by subjecting the core sample to pressure cycling. Pore volume changes during such pressure cycling are measured. Pore compressibility is determined from a plot of the measured pore volume change versus pressure. The core sample is scanned with X-rays at least once for each pressure cycle and a computed tomographic image is produced. From the plurality of produced images, a determination is made of the pressure at which fracturing initiates and of the location or locations within the sample at which fracturing occurs.

U.S. Pat. No. 4,782,501 issued Nov. 1, 1988 to Dixon discloses a method for determining the porosity and pore compressibility of a core sample of a porous media by the use of X-ray scanning in the presence of confining pressure. The porosity of the core sample is determined at atmospheric reference pressure (i.e. zero confining stress). The sample is then saturated with a fluid of predetermined X-ray attenuation coefficient. The fluid saturated sample is placed in a confining pressure cell and scanned with X-rays at a plurality of points along the sample. A first set of computed tomographic images are produced at the plurality of points along the sample. A first set of computed tomographic images are produced at the plurality of points along the sample. From these images, an X-ray attenuation coefficient at zero confining stress is determined. The pressure is then increased within the cell to provide confining stress to the sample. The sample is then scanned with X-rays at a plurality of points along the sample. A second set of computed tomographic images are produced at said plurality of points along the sample for the confining stress. From these images, an X-ray attenuation at confining stress is determined. Porosity is then determined at confining stress from the determinations of sample porosity at zero confining stress, saturating fluid X-ray attenuation coefficient, sample X-ray attenuation coefficient at zero confining stress, and sample X-ray attenuation coefficient at confining stress.

SUMMARY OF THE INVENTION

In accordance with the present invention, a method is provided for determining the relative Compton scattering and photoelectric contributions to the total X-ray attenuation measurements on core samples of earth materials using two or more X-ray scanning energies, and for calculating bulk density of the scanned material, using the difference in attenuation between X-rays of two differing energies and the measured X-ray attenuation for one of the X-ray energies.

More particularly, a first set of material samples are selected with differing densities and having atomic numbers such that X-ray attenuation takes place therein primarily due to Compton scattering. These samples are scanned with X-rays of two different energies and first X-ray attenuations are measured attributable to Compton scattering attenuation. Bulk densities are measured for such samples. The relationship of these X-ray attenuation measurements to bulk density is determined at each of the x-ray energies. Thereafter, a second set of material samples are selected with differing densities and having atomic numbers contributing to both Compton scattering and photoelectric attenuation of X-rays. These samples are scanned with X-rays of two different energies and X-ray attenuations attributable to both Compton scattering and photoelectric X-ray attenuations are measured. Bulk densities of these samples are measured. The Compton scattering contributions to the X-ray attenuation measurements of the second set of samples are calculated from bulk density and the determined relationship of X-ray attenuation measurements to bulk density for the first set of samples. The photoelectric contribution to the X-ray attenuation measurements of the second set of samples is calculated by subtracting the calculated Compton scattering attenuation from the X-ray attenuation measurements for the second set of samples. The change in the measured X-ray attenuations between the X-ray energies and the measured X-ray attenuation for one of the X-ray energies can then be used to determine bulk density of a sample of interest.

DESCRIPTION OF THE PREFERRED EMBODIMENT

Figure 1:
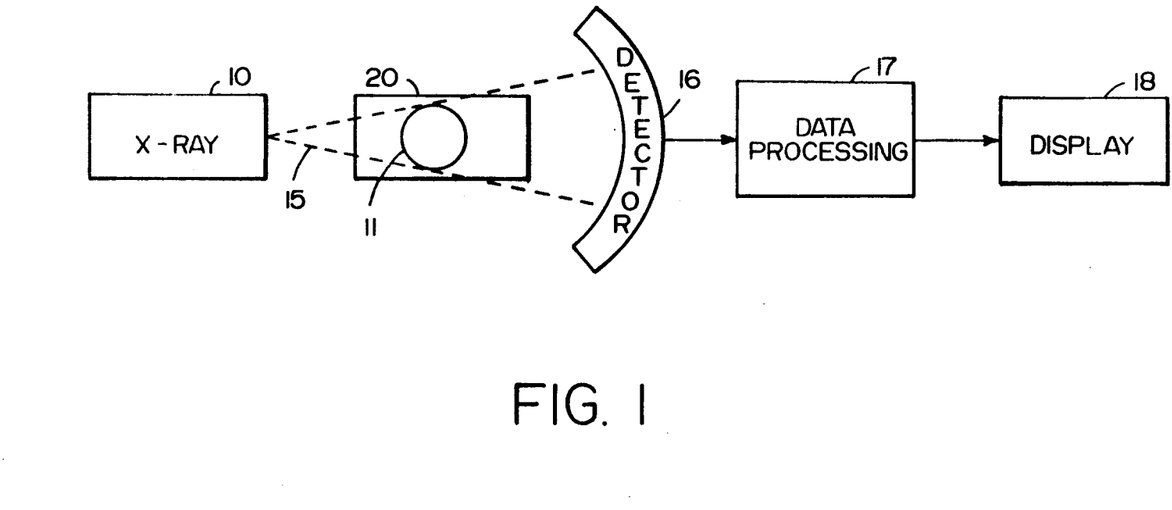
FIG. 1 is a pictorial view of a CT scanning system for use in scanning a material sample with X-ray energy.

Before describing the method of the present invention for the dual energy X-ray scanning of a material sample and the use of the X-ray attenuation measurements from such scanning to calculate bulk density, a brief description will be set forth of a CT scanning system which may be employed in the carrying out of such X-ray scanning and attenuation measurements taken in conjunction with FIG. 1.

Referring now to FIG. 1, X-ray energy provided by the X-ray tube 10 passes through the core sample 11 and falls on the detector array 16. Rotation of the core sample within the X-ray fan bean 15 is provided by a gantry 20. In an alternative embodiment, the core sample 10 may remain stationary and the gantry may be used to rotate the X-ray tube 10 and detector 16 about the core sample. In medical applications, CT scanning rates are used in the order of 2 to 9 seconds. However, patient dose limitations are of no concern in the present application and scan times of the core sample can be up to one minute per scan, or even longer, if desired. The output of the detector array 16 is passed through the data processor 17 to the display 18. After a desired number of scans are completed for a core sample slice, the sample is indexed one slice-width through the X-ray fan beam to place the next adjacent sample slice within the path of the X-ray fan beam. In this manner, a 3-D tomographic presentation is made on the display 18 of the entire sample by compositing the cross-sectional view of each of the scan slices.

A particularly suitable X-ray tube 10 used for CT imaging is the Elscint Excel 2002 translate-rotate body scanner with a Telefunken C-6000 stationary anode-cathode X-ray tube and 280 cadmium tungstate scintillation detectors coupled to solid state photodiodes. The peak X-ray acceleration voltage is 140kV at 40.0 mA. The spatial resolution is 20 line pairs per cm. The pixel (picture element) size at Zoom 1 (512×512) ranges from 0.265 mm to 0.94 mm and at Zoom 4 (512×512) ranges from 0.065 mm to 0.23 mm varying with scan and circle diameter and reconstruction zoom factor.

A particularly suitable detector array 16 for use in the present invention for a 100 micron resolution would comprise a 1024×1 linear array of photodiodes on a 0.001 inch center-to-center spacing with pixel (picture element) apertures of 0.001 inch by 0.1 inch. An example of such an array is the Reticon 1024S/fiber optic faceplate. For a lower 250 micro resolution, a 200×1 linear array of photodiodes on a 0.01 inch center-to-center spacing with pixel aperatures of 0.01 inch to 0.01 would be suitable. An example of such an array is that used in digital mammography equipment supplied by Bio-Imaging Research, Inc. Optically coupled to the input surfaces of the photodiode arrays are scintillation arrays comprised of a plurality of discrete scintillators having X-ray sensitive fluorescent materials individually and optically coupled to the input surfaces of the discrete photodiodes. Such materials may comprise $CdWo_4$, $C_5I$, GdOBr or LaOBr, among others. Such combination of scintillators and photodiodes provides for a complete scintillation counter. The photodiodes provide electrical signals whose heights are proportional to the X-ray energy falling upon the surfaces of the scintillators. After suitable amplification, the signals are digitized for use in producing a desired tomographic display.

The recorded digital image is composed of individual image units arranged in a matrix. Computer tomography images consist of maps of linear X-ray attenuation coefficients within the object being imaged. On standard black and white images, each pixel contains discrete information that corresponds to a spectrum of tonal values on a greyness scale ranging from black (DN=225) to white (DN=0). Similarly, CT image pixels are assigned density values on the Hounsfield scale ranging from low density ($-1000$) to high density ($+3095$).

For a more detailed description of CT scanning systems which may be utilized in the method of the present invention, reference may be made to each of the aforementioned U.S. patents and the referenced Journal of Petroleum Technology article, the teachings of which are incorporated herein by reference.

Conventionally, in medical CT scanning, a water sample is used as an X-ray attenuation standard. When higher attenuation core samples of each materials are scanned, secondary standards are utilized as reference attenuating media. This reference material must be of uniform composition and density and should exhibit attenuation characteristics close to that of the material to be scanned. Examples of such reference materials are aluminum and fused quartz. Fused quartz is uniform in composition and has density and X-ray attenuation close to that of many sandstones. For solid materials (sandstones, fused glass beads, quartz and aluminum) there is a single linear function relating measured attenuation (CT number) to bulk density. This is because such solid materials, as well as water, are composed of atoms having relatively low atomic numbers which cause such materials and water to exhibit low photoelectric attenuation. Consequently most of the X-ray attenuation results from Compton scattering resulting in the simple linear response function of attenuation versus density. Bulk density can accordingly be calculated from single energy X-ray attenuation measurements using this simple linear response function.

However, as the atomic number of a material increases, such as with chlorides, bromides and iodides, the photoelectric contribution to X-ray attenuation increases. That is, X-rays are absorbed by materials according to the photoelectric effect as well as due to Compton scattering, and the photoelectric absorption increases with increase in the atomic number of the material of the sample. Even though the total attenuation by a given material remains a simple linear response function of the incident energy, the slope of such function increases with increasing photoelectric contribution to total attenuation. Consequently material samples having substantial photoelectric contribution cannot be accurately described by a linear response function having a single slope, but must be calibrated against a material sample of similar lithology and composition. The single energy X-ray attenuation measurement for calculating density therefore requires that appropriate standards be made available to characterize the response curve and that there be sufficient knowledge of the material to characterize it as to composition; (i.e. effective atomic number). Inability to identify the composition of a material to be scanned thereby severely limits the usefullness of the single energy X-ray scan. Many core samples from earth formations are inhomogenous, containing heavier elements such as anhydrite or dispersed pyrite. It is therefore a specific object of the present invention to overcome this limitation of the single energy X-ray scan as to material composition. The method of the present invention achieves such objective through the use of two or more X-ray scans of material samples, employing X-rays of differing energies and the use of the resulting attenuation measurements to accurately describe the relative photoelectric and Compton scattering contributions of a particular material. This allows the calculation of bulk density for such earth materials as limestone and dispersed pyrite sandstone (which exhibit high photoelectric attenuation) in addition to clean sandstone (low photoelectric attenuation). Such a method for utilizing X-ray scanning accommodates for changes or non-uniformity in the chemical composition of a material sample, which is critical to application to a wide range of core samples taken from subterranean earth formations containing the heavier minerals for the purpose of characterizing possible hydrocarbon (i.e. oil or gas) reservoirs.

Scanning a material sample with two X-ray energies, for purposes of example, results in the following attenuation expressions in terms of CT numbers for photoelectric and Compton scattering contributions to the total measured X-ray attenuation:

$$CT_t^{e1} = CT_p^{e1} + CT_c^{e1} \tag{1}$$

and $$CT_t^{e2} = CT_p^{e2} + CT_c^{e2}, \tag{2}$$

where the superscripts indicate the scanning energies e1 and e2 and the subscripts refer to total attenuation t, and the photoelectric p and Compton scattering c contributions to the total attenuation.

Figure 2:
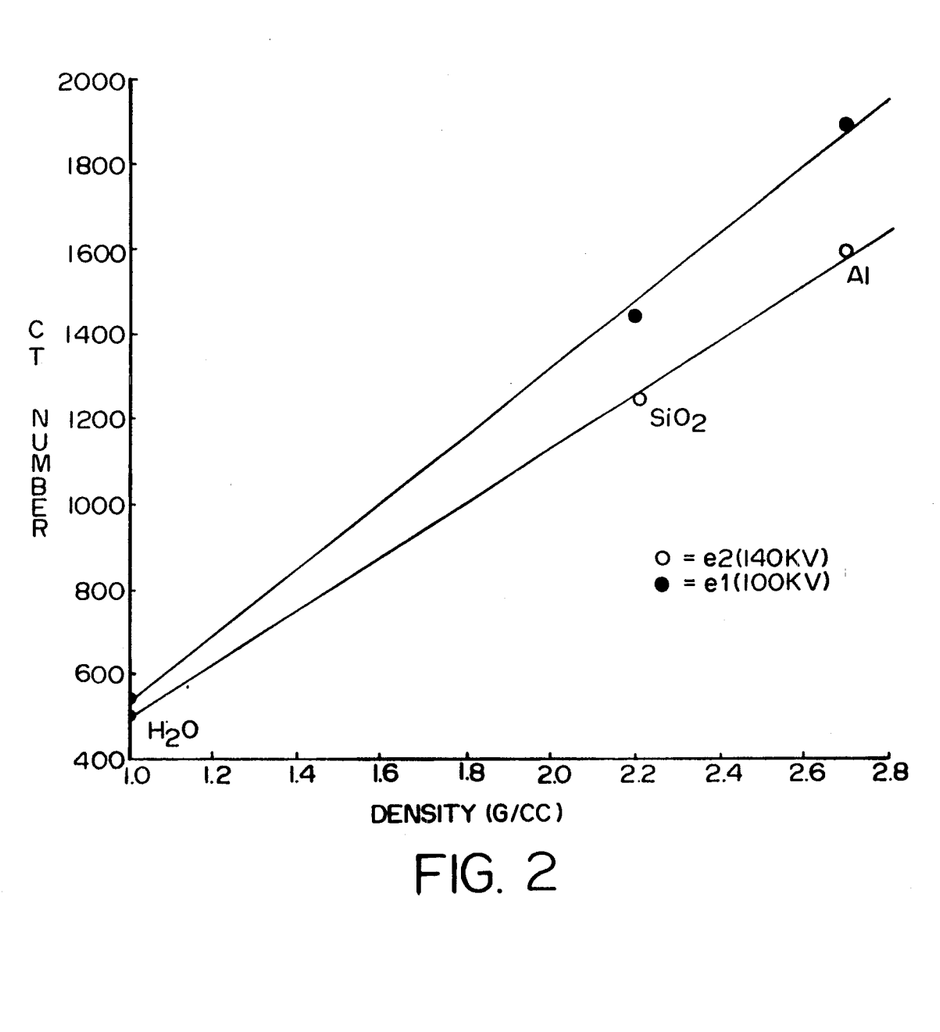
FIGS. 2-5 are plots of X-ray attenuation measurements made by the CT scanning system of FIG. 1 in accordance with the method of the present invention for determining the photoelectric and Compton scattering contributions to total X-ray attenuation as well as bulk density.

Water, quartz and aluminum standards are, among others, composed of elements of low atomic number and in this energy range will attenuate X-rays primarily by Compton scattering which can be described as a linear function of the bulk density P of the material scanned at X-ray energies of 100 KV and 140 KV as shown in FIG. 2; that is, $CT_p \approx 0$ for these materials.

The functional description of the attenuation response of these materials may be used to approximate the X-ray attenuation arising from Compton scattering of other (non-standard) materials as follows:

$$CT_c^{e1} = (a1)(\rho) - b1 \qquad (3)$$

and $$CT_c^{e2} = (a2)(\rho) - b2 \qquad (4)$$

where a1, a2, b1 and b2 are constants defining the linear relationship of equations (1) and (2) above and $\rho$ is the bulk density of the material. For the materials of FIG. 2, that is, materials having low atomic numbers and hence attenuating X-rays principally due to Compton scattering, the linear response functions of equations (3) and (4) become:

$$CT_c^{100KV} = 797.541\rho - 269.498 \qquad (5)$$

and $$CT_c^{140KV} = 636.550\rho - 142.080 \qquad (6)$$

Figure 3:
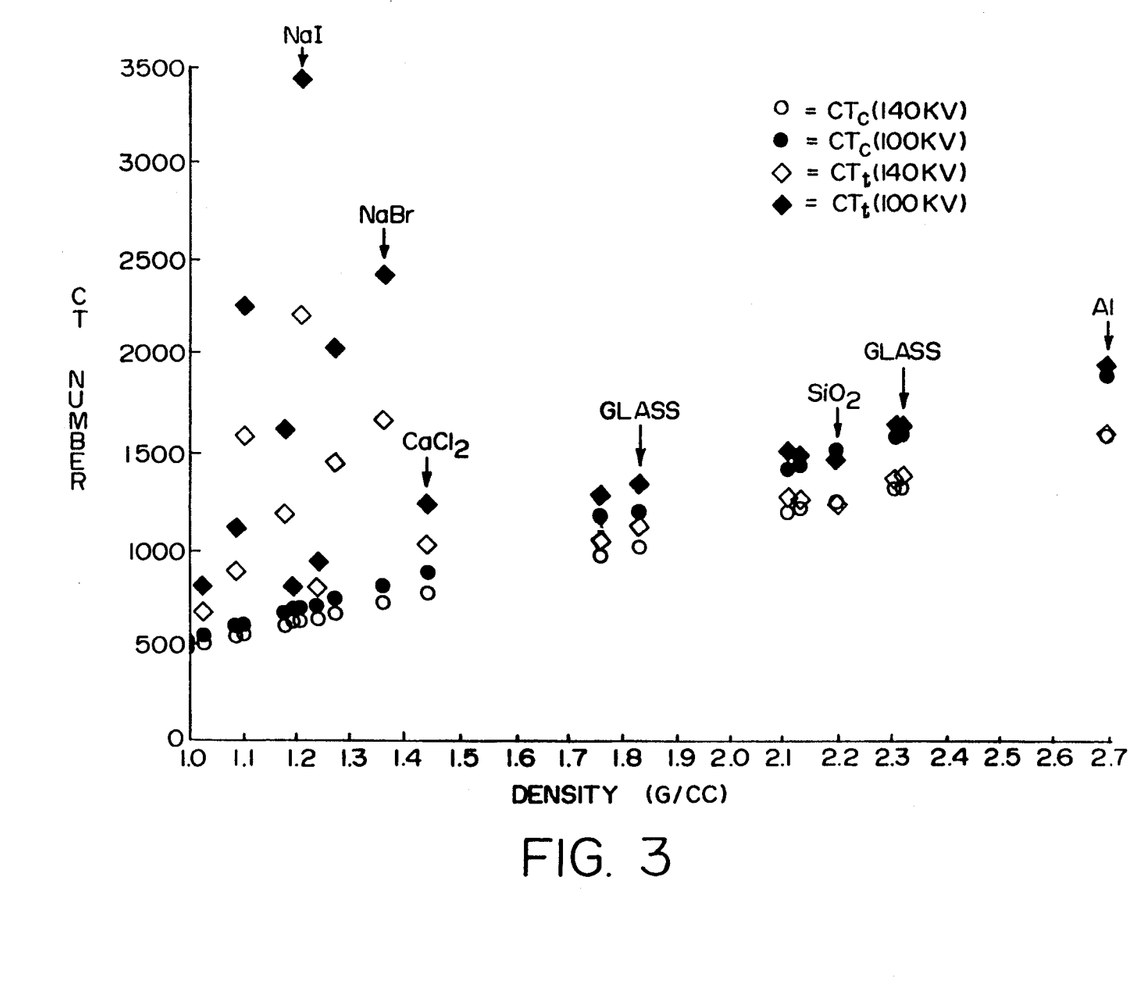

The total CT attenuation of several materials measured at 100 KV and 140 KV are listed in Table 1. Such total CT attenuation and the attenuation $CT_c$ attributed to Compton scattering as calculated from eqs. (5) and (6) are plotted in FIG. 3.

Rearranging the terms of equations (1) and (2) the photoelectric contribution $CT_p$ for materials having higher atomic numbers may be calculated as follows:

$$CT_p^{e1} = CT_t^{e1} - CT_c^{e1} \qquad (7)$$

and $$CT_p^{e2} = CT_t^{e2} - CT_c^{e2}. \qquad (8)$$

Figure 4:
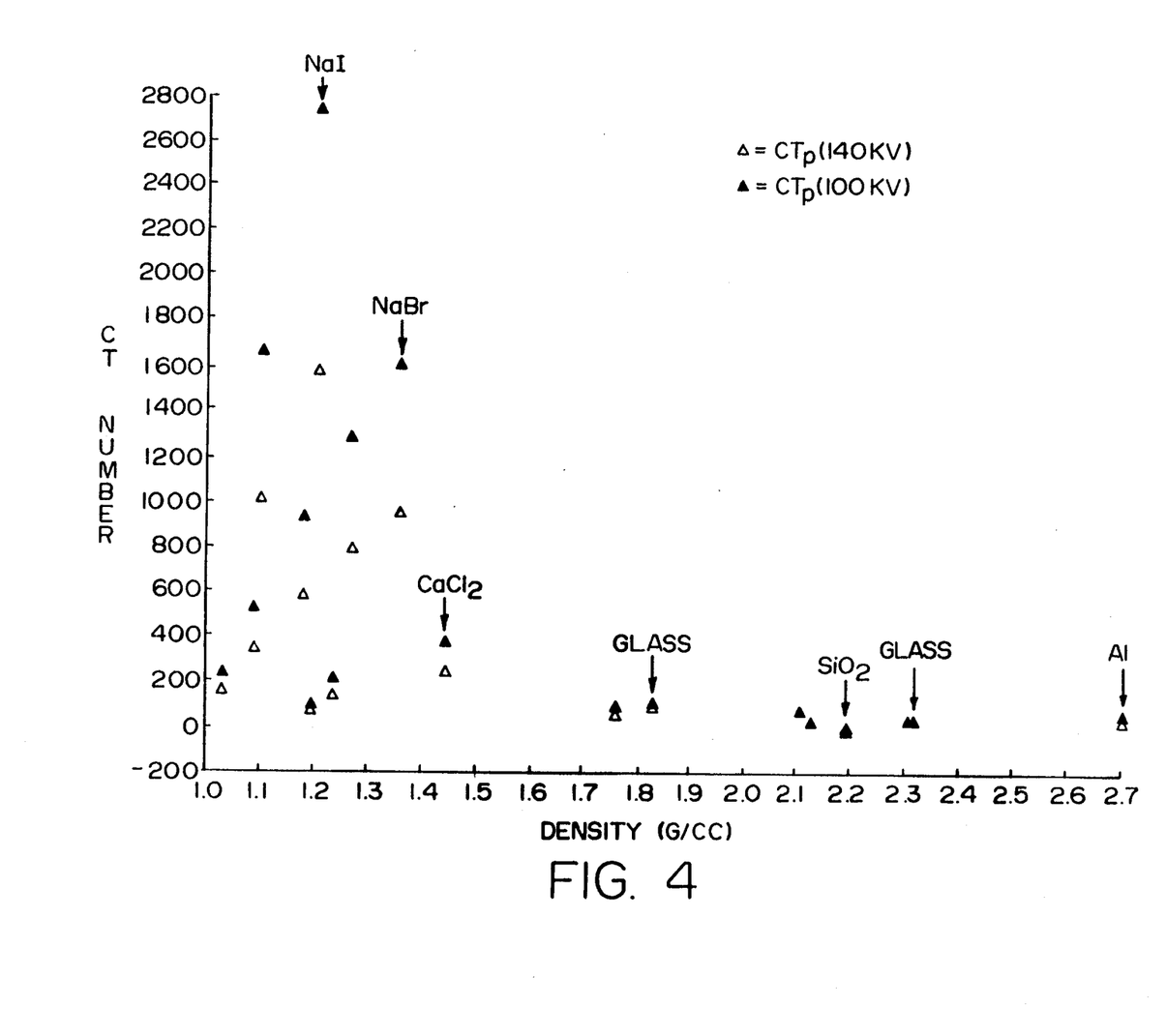

The photoelectric contributions to the total attenuations listed in Table 1 have been calculated from eqs. (7) and (8) and are plotted in FIG. 4 (only a few of the materials being identified by name or symbol).

TABLE 1

| Material | Density (g/cc) | CT # (140KV) | CT # (100KV) |
|---|---|---|---|
| 1. H₂O | 1.0000 | 500.0 | 540.0 |
| 2. NaBr | 1.0300 | '678.7 | 801.3 |
| 3. NaBr | 1.0900 | 901.2 | 1135.6 |
| 4. NaI | 1.1030 | 1581.8 | 2268.9 |
| 5. NaBr | 1.1800 | 1200.2 | 1609.9 |
| 6. NaCl | 1.1970 | 684.9 | 777.9 |
| 7. NaI | 1.2000 | 2203.4 | 3429.4 |
| 8. CaCl₂ | 1.2378 | 799.4 | 943.5 |
| 9. NaBr | 1.2700 | 1450.3 | 2032.2 |
| 10. NaBr | 1.3600 | 1666.4 | 2412.7 |
| 11. CaCl₂ | 1.4428 | 1029.0 | 1258.1 |
| 12. Fused glass beads 1A | 1.7600 | 1035.7 | 1221.9 |
| 13. Fused glass beads 5 | 1.8300 | 1112.6 | 1298.2 |
| 14. Fused glass beads 2A | 2.1100 | 1267.6 | 148.5 |
| 15. Kel-F teflon | 2.1300 | 1240.3 | 1461.7 |
| 16. Fused quartz | 2.1960 | 1241.5 | 1445.4 |
| 17. Fused glass beads 4 | 2.3100 | 1358.3 | 1616.0 |
| 18. Fused glass beads 3 | 2.3200 | 1375.2 | 1612.2 |
| 19. Al | 2.7000 | 1588.2 | 1918.2 |

All CT values shifted by 1000 to elimate negative signs.

Figure 5:
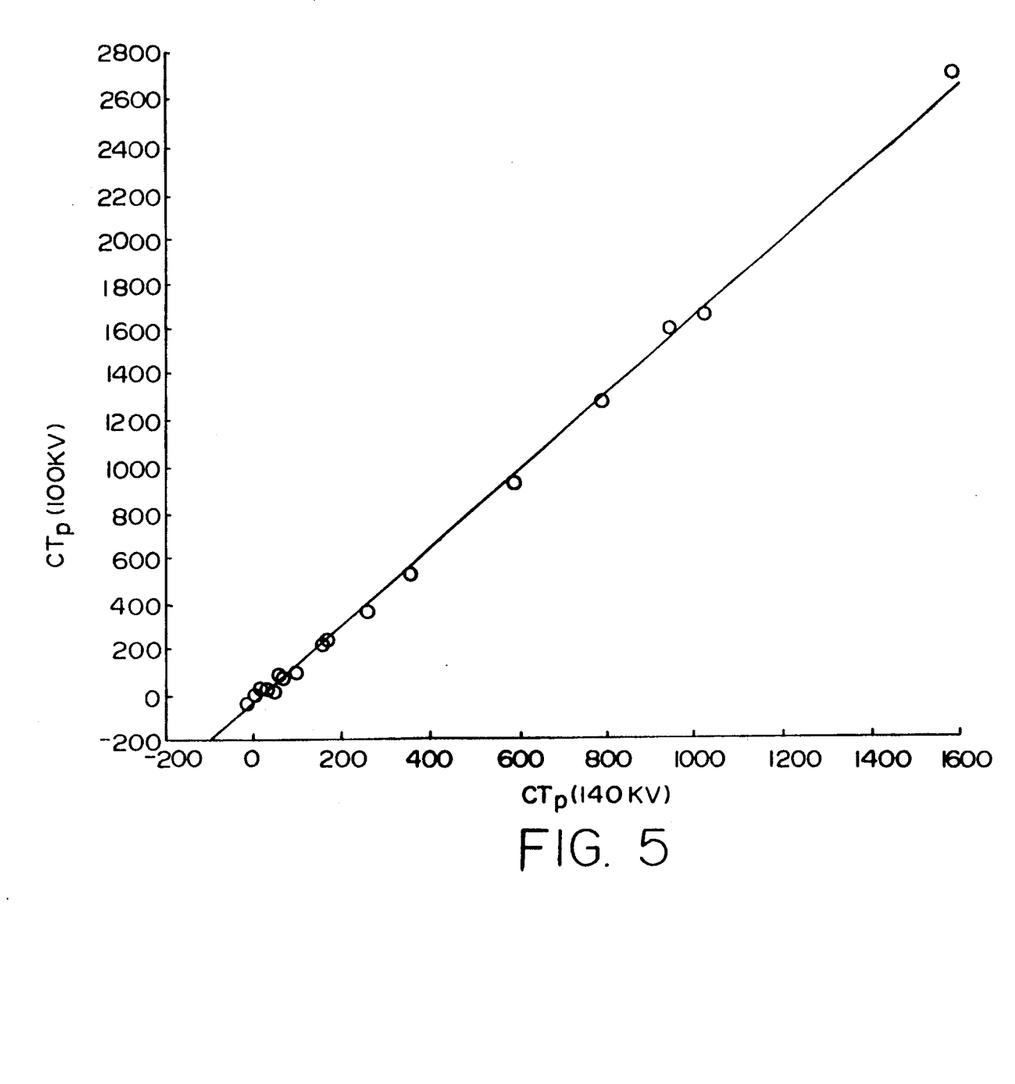

Plotting these photoelectric contributions to attenuation at one energy with respect to another energy reveals a linear relationship shown in FIG. 5 having the general expression:

$$CT_p^{e1} = (c)CT_p^{e2} - d \qquad (9)$$

where c and d are constants defining the linear relationship. This linear relationship of the plot of FIG. 5 is expressed as:

$$CT_p^{100KV} = (1.71)CT_p^{140KV} - 28.047 \qquad (10)$$

subtracting equations (1) and (2) yields:

$$\Delta CT_t = CT_p^{e1} - CT_p^{e2} + CT_c^{e1} - CT_c^{e2} \qquad (11)$$

where $\Delta CT_t$ is the total difference in measured CT number measured with respect to scanning energies e1 and e2 i.e., $\Delta CT_t = CT_t^{e1} - CT_t^{e2}$. Subtracting equation (4) from equation (3) and substituting into eq. (11) yields:

$$\Delta CT_t = CT_p^{e1} - CT_p^{e2} + a3\rho - b3 \qquad (12)$$

where
a3 = a1 − a2 and
b3 = b1 − b2.

Using the expressions of equations (6) and (5) for equations (4) and (3) respectively, equation (12) becomes $$\Delta CT_t = CT_p^{100KV} - CT_p^{140KV} + 160.991\rho - 127.416. \qquad (13)$$

Substituting equations (9), (8) or (7) and (4) or (3) sequentially into equation (12) and rearranging terms yields the following general bulk density expression:

$$\rho = (\Delta CT_t - f(CT_t^{e'}) + g)/h \qquad (14)$$

where f, g and h are constants and $CT_t^{e'}$ is the attenuation measured at one of the energies e1 or e2.

With e2 being the selected energy for e1, equations (10), (8) and (6) are substituted into (13) and terms rearranged, equation (14) becomes:

$$\rho = (\Delta CT_t - 0.07086\ CT_t^{140KV} + 54.783)/-290.068 \qquad (15)$$

Thus, given the constants f, g, and h determined in solution of equation (14) with respect to known sample materials, the bulk density $\rho$ of a sample of interest can be calculated directly upon measurement of the total attenuation $CT_t$ at two energies e1 and e2. As an example a berea core sample lists a measured CT value of 1208.30 CT units at 140 KV scanning energy and a measured CT value of 1415.30 units at 100 KV scanning energy. The change in measured CT number is 207. The calculated density from Equation (15) becomes:

$$\rho = [207 - 0.7086\ (1208.3) + 54.783]/-290.068 = 2.05 \qquad (16)$$

Alternatively, with e1 being the selected energy for e', equations (10), (7) and (5) are substituted in equation (13) and terms rearranged, equation (14) becomes:

$$\rho = (\Delta CT_t - 0.4147\ CT_t^{100KV} + 32.073)/-169,258$$

and (17)

calculated density becomes:

$$\rho = [207 - 0.4147\ (1415.30) + 32.073]/-169.25 = 2.05. \qquad (18)$$

Having now described the method of the present invention in identifying the relative photoelectric and Compton scattering contributions to total X-ray scanning attenuation, and the use of the change in total X-ray attenuation along with the total attenuation at one of the energies to calculate bulk density, it is to be understood that various modifications and changes may be made to such method without departing from the spirit and scope of the invention as set forth in the appended claims.

We claim:

1. A method for determining the bulk density of a sample of interest, comprising the steps of:
   (a) selecting a first plurality of samples of a first variety of materials having different known densities, the materials of said first plurality having relatively low atomic numbers, such that said samples attenuate X-rays incident thereon due to Compton scattering;
   (b) irradiating each of said first plurality of samples in turn with at least first and second beams X-rays, from sources emitting beams of X-rays at differing energies;
   (c) employing detector means to collect X-rays of said beams passing through said samples;
   (d) measuring amounts of X-rays collected by the detector means to determine the attenuation of the beams of X-rays of differing energies by each of the first plurality of samples;
   (e) determining the parameters defining a linear relation between the attenuation of the X-rays due to Compton scattering in the first plurality of samples and the bulk densities of the samples;
   (f) selecting a second plurality of samples of a second variety of materials having different known densities, the materials of said second plurality of samples having relatively high atomic numbers such that said second plurality of samples attenuate X-rays incident thereon due to both Compton scattering and photoelectric absorption;
   (g) irradiating each of said second plurality of samples in turn with at least first and second beams of X-rays from sources emitting beams of X-rays at differing energies;
   (h) employing detector means to collect X-rays passing through the samples of said second plurality of samples;
   (i) measuring the amount of X-rays collected by the detector means to determine the attenuate of the beams of X-rays of differing energies of each of the second plurality of samples;
   (j) determining parameters defining a linear relation between the attenuation of X-rays due to photoelectric absorption in the second plurality of samples and the energy of the X-rays;
   (k) using the linear relation between the attenuation of X-rays due to photoelectric absorption and the energy of the X-rays determined in step (j), and the linear relationship between the absorption of X-rays due to Compton scattering in a material sample and the bulk density of the material of the sample determined in step (e), to define a linear relation defining the bulk density of the materials of the second plurality of samples as a function of the measured total attenuation of the two beams X-rays at two different energies by the given material; and
   (l) determining the bulk density of a section of a sample of interest by:
      (1) irradiating the sample of interest with first and second beams of X-rays from sources emitting beams of X-rays at two differing energies;
      (2) employing detector means to collect X-rays passing through the section of the sample of interest;
      (3) measuring the amount of X-rays collected to determine the total attenuation of the beams of X-rays by the section of the sample of interest; and
      (4) employing the relationship defined in step (k) to determine the bulk density of the section of the sample of interest;
   (m) performing said step (l) with respect to a number of sections of the sample of interest;
   (n) carrying out said steps (l) and (m) repetitively with the source and detector disposed in differing positions with respect to the sample of interest; and
   (o) generating a computed tomographic image of a cross-section of the sample of interest, employing the values for the bulk density $\rho$ of the plural portions of the sample of interest which are determined in each performance of steps (l), (m) and (n).

2. The method of claim 1, wherein said step (e) of determining parameters defining a linear relation between the attenuation of the beam of X-rays of differing energies by each of the first plurality of samples due to Compton scattering is carried out by determining values for the parameters a1, a2, b1 and b2 in the following expressions:

$$CT_c^{e1} = (a1)\rho - b1; \text{ and}$$

$$CT_c^{e2} = (a2)\rho - b2;$$

in which:
   $CT_c^{e1}$ and $CT_c^{e2}$ are quantities indicative of the attenuation of X-rays at energies e1 and e2 due to Compton scattering in particular ones of said first plurality of samples; and
   $\rho$ represents the bulk density of the corresponding sample.

3. The method of claim 2, wherein said step (j) of determining parameters defining a linear relation between the attenuation of beams of X-rays of two different energies due to photoelectric absorption in the materials of said second plurality of samples is performed by determined values for the parameters c and d in the following expression:

$$CT_p^{e1} = (c)(CT_p^{e2}) - d,$$

in which:
   $CT_p^{e1}$ and $CT_p^{e2}$ are quantities indicative of attenuation of X-rays at energies e1 and e2 due to photoelectric absorption in particular ones of said second plurality of samples, and in which $CT_p^{e1}$ and $CT_p^{e2}$ are determined by solution of the following equation:

$$\Delta CT_t = CT_p^{e1} - CT_p^{e2} + a3(\rho) - b3,$$

in which:
   $\Delta CT_t$ is the difference between measured values representing the total X-ray attenuation of the two beams of X-rays of energies e1 and e2 by ones of said second plurality of samples,
   a3 = a1 − a2, and
   b3 = b1 − b2.

4. The method of claim 3, wherein said step (l) of determining the bulk density $\rho$ of the sample of interest is performed by solution of the following linear equation defined in step (k):

$$\rho = (\Delta CT_t - f(CT_t^{e1}) + g)/h,$$

in which:
  f, g, and h are constants determined in step (k) with respect to said second plurality of samples of materials of known density ρ, with respect to a beam X-rays of a particular energy e';
  $\Delta CT_t$ is the difference between measured values representing the total X-ray attenuation of two beams of X-rays of different energies e1 and e2 by the sample of interest, measured in step (1)(3); and
  $CT_t^{e'}$ is a measured value representing the attenuation of one of the two beams of X-rays of energy e' by the sample of interest.

5. The method of claim 1, wherein said detector means comprises a number of separate detector elements which simultaneously detect X-rays passing through plural sections of the sample of interest.

6. A method for providing an image of a section of a sample of interest in which the elements of the image correspond to the bulk density ρ of corresponding portions of the sample of interest, by measuring the attenuation of X-rays by said sample, said method comprising performance of preliminary steps (a)-(c) as follows:
  (a) determining parameters defining at least one first linear relation describing the attenuation of X-rays due to Compton scattering in a sample as a function of the density of the sample, by:
    (i) irradiating a first plurality of samples of materials of relatively low atomic weight and known bulk density with a first beam of X-rays from a source of X-rays of a first energy;
    (ii) irradiating said first plurality of samples with a second beam of X-rays from a source of X-rays of a second energy;
    (iii) collecting X-rays of said first and second beams passing through said first plurality of samples on detector means;
    (iv) determining the attenuation of the X-rays of the first and second beams by the first plurality of samples; and
    (v) determining the parameters in said at least one first linear relation responsive to the measured attenuation of the X-rays by the first and second samples;
  (b) determining parameters in a second linear relation defining the attenuation of X-rays at two different energies due to photoelectric absorption as a function of the energy of the X-rays by:
    (i) irradiating a second plurality of samples of materials of relatively high atomic weight and known bulk density with a first beam of X-rays from a source of X-rays of a first energy;
    (ii) irradiating said second plurality of samples with a second beam of X-rays from a source of X-rays of a second energy;
    (iii) collecting X-rays of said first and second beams passing through the samples of second plurality on detector means;
    (iv) determining the attenuation of the X-rays of the first and second beams by the second plurality of samples; and
    (v) determining the parameters in said second linear relation responsive to the measured attenuation of the X-rays by the second plurality of samples;
  (c) employing the constants determined in steps (a) and (b) to determine parameters defining a linear relation describing the bulk density ρ of each of said second plurality of samples in relation to the measured attenuation of the first and second beams of X-rays thereby;
  (d) thereafter determining the bulk density ρ of a plurality of sections of the sample of interest by:
    (i) irradiating the sample of interest with a first beam of X-rays from a source of X-rays of a first energy;
    (ii) irradiating the sample of interest with a second beam of X-rays from a source of X-rays of a second energy;
    (iii) collecting X-rays of said first and second beams passing through the sections of the sample of interest on detector means;
    (iv) determining the attenuation of the X-rays of the first and second beams by corresponding sections of the sample of interest; and
    (v) employing the measured attenuation of the first and second beams to solve the linear relation defined in step (c) for the bulk density ρ of each section of the sample of interest;
  (e) performing said step (d) repetitively with the source and detector disposed at slightly different positions with respect to the sample of interest during each performance of steps (d)(i) and (d)(ii); and
  (f) employing the values for the bulk density ρ of the sections of the sample determined in each performance of step (d)(v) to generate a computed tomographic image of the section of the sample of interest.

7. The method of claim 6 wherein said linear relation defined in step (c) takes the form of the following equation:

$$\rho = (\Delta CT_t - fCT^{e'} + g)/h$$

wherein:
  ρ = bulk density of a particular sample;
  $\Delta CT_t$ = quantity representing the difference in measured attenuation of X-rays of two different energies by said particular sample;
  $CT^{e'}$ = quantity representative of the measured attenuation of X-rays of one of said energies e' by said particular sample; and
  f, g, and h are parameters determined in said step (c) with respect to said second plurality of samples.

8. The method of claim 6, wherein said at least one linear relation defining the attenuation of X-rays due to Compton scattering in said first plurality of samples of step (a) takes the form:

$$CT^{e'} = (a')\rho - b'$$

wherein:
  $CT^{e'}$ = a quantity representing the total attenuation of a beam of X-rays of energy e' by a particular one of said first samples due to Compton scattering;
  a' and b' = parameters dependent on the energy e' of the beam of X-rays; and
  ρ = measured bulk density of the particular sample.

9. The method of claim 6, wherein said linear relation between attenuation of X-rays at two different energies e1 and e2 due to photoelectric absorption of step (b) takes the form:

$$CT^{e1} = (c)CT_p^{e2} - d$$

wherein:

$CT_p^{e'}$ = a quantity representing attenuation of X-rays of a particular energy e' due to photoelectric absorption in a sample of a material; and c and d are parameters which do not vary with the material of the sample.

10. The method of claim 6 wherein said detector means comprises a number of separate detector elements for simultaneously detecting X-rays passing through a like number of sections of the sample of interest.

* * * * *

UNITED STATES PATENT AND TRADEMARK OFFICE
CERTIFICATE OF CORRECTION

PATENT NO. : 5,063,509

DATED : November 5, 1991

INVENTOR(S) : Coles et al.

It is certified that error appears in the above-identified patent and that said Letters Patent is hereby corrected as shown below:

Col. 9, line 17: Insert --of-- before "X-rays,"

Col. 9, line 45, "attenuate" should read --attenuation--

Col. 9, line 46, "of each" should read --by each--

Col. 9, line 62: Insert --of-- before "X-rays,"

Col. 10, line 45, "determined" should read --determining--

Col. 11, line 10, Insert --of-- before "X-rays"

Col. 12, line 45, Insert --a-- before "quantity"

Col. 12, line 48, Insert --a-- before "quantity"

Col. 12, line 58: "$CT^{e'}$" should read --$CT_c^{e'}$--

Col. 12, line 61, "$CT^{e'}$" should read --$CT_c^{e'}$--

Col. 13, line 7, "$CT^{el}$" should read --$CT_p^{el}$--

Signed and Sealed this

Ninth Day of March, 1993

Attest:

STEPHEN G. KUNIN

*Attesting Officer*    *Acting Commissioner of Patents and Trademarks*